United States Patent
Noda et al.

(10) Patent No.: US 10,274,506 B2
(45) Date of Patent: Apr. 30, 2019

(54) AUTOMATIC ANALYTICAL APPARATUS (71) Applicant: HITACHI HIGH-TECHNOLOGIES CORPORATION, Tokyo (JP)

(72) Inventors: Kazuhiro Noda, Tokyo (JP); Yoichiro Suzuki, Tokyo (JP)

(73) Assignee: Hitachi High-Technologies Corporation, Tokyo (JP)

(*) Notice: Subject to any disclaimer, the term of this patent is extended or adjusted under 35 U.S.C. 154(b) by 0 days.

(21) Appl. No.: 15/111,623

(22) PCT Filed: Jan. 19, 2015

(86) PCT No.: PCT/JP2015/051158
§ 371 (c)(1),
(2) Date: Jul. 14, 2016

(87) PCT Pub. No.: WO2015/111526
PCT Pub. Date: Jul. 30, 2015

(65) Prior Publication Data
US 2016/0334431 A1 Nov. 17, 2016

(30) Foreign Application Priority Data
Jan. 27, 2014 (JP) ................................. 2014-012084

(51) Int. Cl.
*G01N 35/04* (2006.01)
*G01N 35/00* (2006.01)
(Continued)

(52) U.S. Cl.
CPC ......... *G01N 35/04* (2013.01); *G01F 23/2928* (2013.01); *G01N 35/0099* (2013.01);
(Continued)

(58) Field of Classification Search
CPC ........................................................ B01L 9/50
See application file for complete search history.

(56) References Cited

U.S. PATENT DOCUMENTS

| 4,595,562 A | * | 6/1986 | Liston | G01N 35/04 |
| | | | | 198/465.1 |
| 4,740,025 A | * | 4/1988 | Nelson | B01L 9/50 |
| | | | | 294/902 |

(Continued)

FOREIGN PATENT DOCUMENTS

| EP | 0 619 476 A1 | 10/1994 |
| EP | 1 353 183 A2 | 10/2003 |

(Continued)

OTHER PUBLICATIONS

International Search Report of PCT/JP2015/051158 dated Apr. 21, 2015.

(Continued)

*Primary Examiner* — Benjamin R Whatley
(74) *Attorney, Agent, or Firm* — Mattingly & Malur, PC (57) ABSTRACT

In the past, when centering the center of a liquid surface and fixation thereof proved difficult during mounting a container into an automatic analytical apparatus, there was sometimes the possibility that the accuracy of checking the liquid surface conditions and the pipetting precision could not be ensured. When this problem occurred, there was the possibility that the reliability of the analysis results would be diminished. Accordingly, an automatic analytical apparatus is provided with a probe for suctioning a liquid to be used in analysis, wherein the apparatus is provided with a transport apparatus for transporting a container accommodating the liquid, and a container-clamping apparatus for clamping the container transported by the transport apparatus. The container-clamping apparatus has a vibration suppression mechanism for retaining the clamped container with an elastic body, and a centering retention mechanism with which centering of the container center can be fixed.

3 Claims, 9 Drawing Sheets

(51) Int. Cl.
*G01N 35/02* (2006.01)
*G01F 23/292* (2006.01)
*B01L 9/00* (2006.01)
*G01F 23/00* (2006.01)

(52) U.S. Cl.
CPC ..... *G01N 35/00732* (2013.01); *G01N 35/025* (2013.01); *B01L 9/50* (2013.01); *G01F 23/0069* (2013.01); *G01N 35/0098* (2013.01); *G01N 2035/0405* (2013.01); *G01N 2035/0412* (2013.01); *G01N 2035/0493* (2013.01); *G01N 2035/0494* (2013.01)

(56) References Cited

U.S. PATENT DOCUMENTS

| | | | | |
|---|---|---|---|---|
| 5,525,298 | A * | 6/1996 | Anami | G01N 35/1079 |
| | | | | 422/533 |
| 5,665,309 | A * | 9/1997 | Champseix | G01N 35/04 |
| | | | | 141/130 |
| 2003/0061911 | A1 | 4/2003 | Niwayama et al. | |
| 2005/0123445 | A1 * | 6/2005 | Blecka | G01N 35/0099 |
| | | | | 422/64 |
| 2013/0082099 | A1 * | 4/2013 | Furrer | G01N 35/00732 |
| | | | | 235/375 |
| 2013/0128035 | A1 * | 5/2013 | Johns | B01D 21/262 |
| | | | | 348/135 |
| 2013/0239527 | A1 | 9/2013 | Clarke et al. | |
| 2013/0315486 | A1 * | 11/2013 | Franz | G01N 21/9027 |
| | | | | 382/190 |

FOREIGN PATENT DOCUMENTS

| | | | |
|---|---|---|---|
| JP | 06-072879 | A | 3/1994 |
| JP | 3343187 | B | 11/2002 |
| JP | 2003-094374 | A | 4/2003 |
| JP | 3688662 | B | 8/2005 |
| JP | 2010-107308 | A | 5/2010 |
| JP | 2010107308 | A * | 5/2010 |
| JP | 2011-252804 | A | 12/2011 |
| JP | 2013-152214 | A | 8/2013 |

OTHER PUBLICATIONS

Extended European Search Report received in corresponding European Application No. 15739796.9 dated Oct. 11, 2017.

* cited by examiner

AUTOMATIC ANALYTICAL APPARATUS

TECHNICAL FIELD

The present invention relates to an automatic analytical apparatus including an imaging device which images liquid in a container containing the liquid or a pipetting device which pipets the liquid.

BACKGROUND ART

Recently, trace pipetting of liquid of a reagent and a sample to be used in an analysis is performed to reduce running cost. To suction trace liquid, it is necessary to grasp an accurate liquid surface height and suction liquid at a fixed position such as a liquid surface position or directly below the liquid surface position. Therefore, it is necessary to grasp the liquid surface height and accurately control a suction probe position and a liquid surface position.

Examples of a method for grasping a liquid surface height include a method for obtaining an image and information on a container containing liquid and liquid in the container by such as a camera or a laser source from the outside of the container and a method for detecting a position of a liquid surface height based on a change in a capacitance when a probe tip and a liquid surface come into contact when the suction probe is moved down in the container.

For example, PTL 1 discloses that a sample checker which irradiates a side wall of a container with a laser source to check a specimen in a blood collection tube includes a chuck mechanism for clamping and fixing the blood collection tube during irradiation of the laser source.

CITATION LIST

Patent Literature

PTL 1: JP 2011-252804 A

SUMMARY OF INVENTION

Technical Problem

As described above, a specimen transport apparatus and an automatic analytical apparatus need to accurately grasp a liquid surface height. However, in the case where blood collection tubes of various diameters are mixedly used, a blood collection tube with a small diameter is less firmly held than a blood collection tube with a large diameter. Therefore, it is assumed that the blood collection tube might be carried in an inclined state or the tube might not be centered since the center of the blood collection tube is varied. For example, if a container is inclined or is not centered when information on a liquid surface height is obtained by a camera and a laser, the liquid surface height information may not be accurately obtained. Further, further, in a pipetting process, since a container is not centered, a liquid surface position is varied, and reproductivity of trace pipetting may not be secured.

In the case where such process failure occurs, a user needs to confirm whether the process is correctly performed, and if the process is affected by which a container is not centered at a correct position, the user needs to instruct to perform the same process to the container one more time, or an operator needs to perform the process. Consequently, a report of an analysis result might be delayed, and reliability of the analysis result might be decreased.

In view of the above issue, an object of the present invention is to provide a container holding device capable of suppressing a backtracking operation by a user, a delay of the result report, and a decrease in reliability of the analysis result by performing a process after a, container is certainly centered. The above object and other objects of the present invention and new characteristics will be clarified by the description herein and attached drawings.

Solution to Problem

Characteristics of the present invention in view of the above issue is as below.

Specifically, a container-clamping apparatus for clamping a container transported by a transport mechanism is included. The container-clamping apparatus includes at least two container holding members, an arm, and a connection member. The container holding members hold a side wall of the container. The arm moves the container holding members toward the container. The connection member connects the arm and the container holding member. At least apart of the container holding member or the connection member is formed of an elastic body.

Advantageous Effects of Invention

According to the present invention, by the above-described configuration, a container is centered which is held by a chuck mechanism. Consequently an accurate liquid surface position can be detected, and highly reproductive liquid pipetting can be realized.

DESCRIPTION OF EMBODIMENTS

Examples based on the present invention will be described below as embodiments of the present invention.

EXAMPLE 1

Figure 1A:
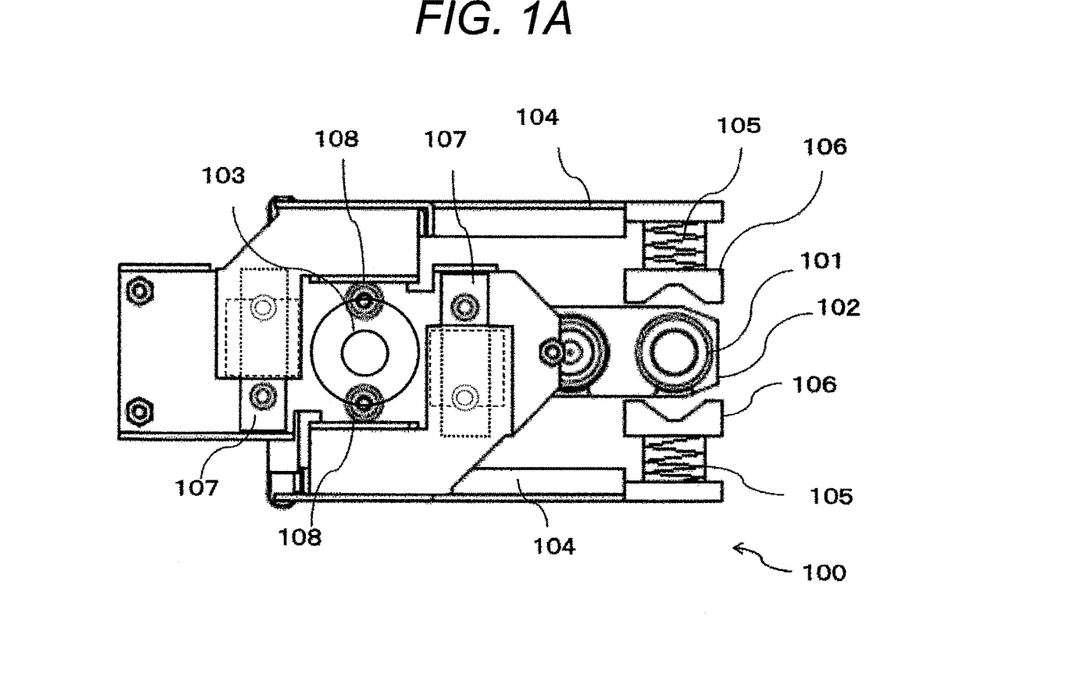
FIG. 1A is a view illustrating a state in which a holder using an arm opening/closing mechanism is opened by a linear movement in an embodiment of the present invention.
Figure 1B:
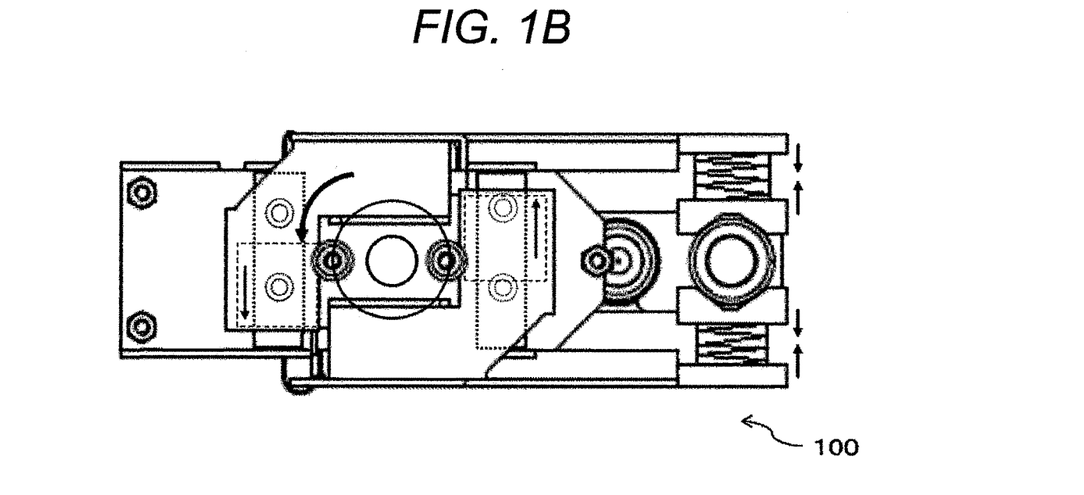
FIG. 1B is a view illustrating a state in which the holder using the arm opening/closing mechanism is closed by a linear movement in the embodiment of the present invention.
Figure 1C:
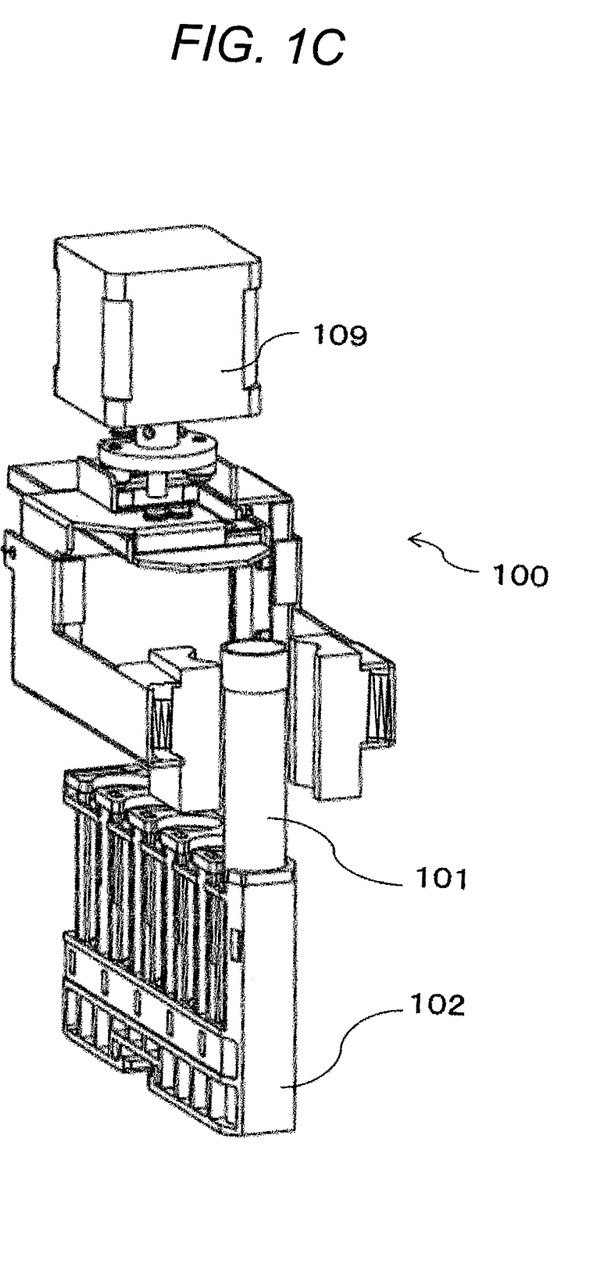
FIG. 1C is an overall view of the holder using the arm opening/closing mechanism by a linear movement in the embodiment of the present invention.

As an embodiment of the present invention, a container holding device 100 using an arm opening/closing mechanism by a liner movement will be described with reference to FIGS. 1A to 1C. FIGS. 1A and 1B are views illustrating the container holder 100 from an upper surface side. FIG. 1A illustrates a state in which the container holder 100 is not holding a container. FIG. 1B illustrates a state in which the container holder 100 is holding the container. FIG. 1C illustrates an overall view of the container holder 100 and a container 101 erected on a rack 102 as an example of a holding target.

A container-clamping apparatus 100 includes an actuator 103, an opening/closing arm 104, an elastic body 105, a container holding member 106, and a linear movement mechanism 107. Power generated by rotation of the actuator 103 is transmitted to the opening/closing arm 104 via a link mechanism 108, and the opening/closing arm 104 opens and closes on right and left sides. At this time, the opening/closing arm 104 linearly drives by the linear movement mechanism 107 so as to open on right and left sides in association with driving of the actuator 103.

The elastic body 105 is provided to each of the opening/closing arms 104 for suppressing vibration and centering a container. Further, the container holding member 106 is provided to a tip of the elastic body 105. Since the container holding member 106 is connected via the elastic body 105, the elastic body is compressed when holding a container (FIG. 1B). Therefore, the container is pushed by the same elastic body from the both sides, and the center of containers having various diameters can be also positioned at a same position. Further, even if a container is inclined, the container can be held upright by applying the same elastic force from both sides of the container.

Further, even if vibration occurs around the container-clamping apparatus 100, the vibration is absorbed by the elastic body 105. Therefore, the vibration is not transmitted to a container held by the container-clamping apparatus 105, and the container can be stably held.

A vibration suppression mechanism is configured as a spring connected to each arm opening/closing mechanism. However, the vibration suppression mechanism may be an elastic body, such as rubber, other than a spring. Further, the container holding member 106 is formed in a block body having a recess such that the member can hold a container having a cylindrical shape. However, the member may have another shape depending on a container shape.

A basic operation of the container-clamping apparatus 100 according to the example will be described next. Here, an operation for holding a test tube mounted on a rack will be described as an example of a holding target container. However, the present invention is not limited to this embodiment.

A detector (not illustrated) is provided near the container-clamping apparatus 100. The detector detects that a container to be held arrives through a lower side of the container-clamping apparatus 100. As the detector, a known detecting means such as a light sensor, an RFID reader, a bar code reader may be used. As detection method, arrival of a specimen container may be detected, and after arrival of the rack 102 is detected, a test tube mounted on the rack 102 may be transported so as to move to an appropriate holding position of the container-clamping apparatus 100.

When the detector detects that the sample container 101 erected on the rack 102 arrives at a holding position, the opening/closing arm 104 shifts to a closed position by which the actuator 103 rotationally drives, and the link mechanism 108 pushing the opening/closing arm 104 on both sides to open moves to a position where the link mechanism 108 does not come into contact with the opening/closing arm. At this time, the actuator 103 is driven by a motor 109. When it is notified that the detector detects a container, the motor 109 rotationally drives the actuator 103.

When the opening/closing arms 104 shift from an open state to a close state, an amount to move in a direction in which the opening/closing arms 104 approach each other is preferably larger than a movement amount needed to cause the container holding member 106 to come into contact with a side surface of a container. Accordingly, in the case of holding the container (as illustrated in FIG. 1B), the elastic body 105 is compressed at all times, and a repulsive force is generated between a side surface of the container and the opening/closing arm. A pair of the opening/closing arms includes the elastic body 105 having an elastic modulus which is the same on right and left sides. Therefore, a container held by the container holding member 106 is pushed by the same force from both sides. Further, since the pair of the opening/closing arms is driven by rotation of an actuator, a driving amount thereof is constant at all times. Therefore, even if a position of the container is deviated, the center of the container can be held and centered at all times at the same position since the container is pushed by the same force from the both sides. Further, the same repulsive force is applied from both sides of the container. Therefore, even if the containers have various diameters, the center of the container can be held at the same position.

Further, the same repulsive force is applied to a side surface of a container held by the container holding member 106 from both sides. Therefore, even if a shaft center of a container is inclined, the container can be held at a correct position, and as illustrated in FIG. 1B, the container can be held at all times at the same position and in the same state.

Further, even if an external vibration of such as device vibration is generated on a lateral direction, the vibration is absorbed by the elastic body 105, and the vibration is not transmitted to the held container.

In the present example, as a container to be held, the sample container 101 is assumed which has a test tube shape and is erected on the rack 102 which can carry a plurality of test containers. However, the container is not limited thereto. A test container carried by a holder which can mount one test tube may be held, and a reagent bottle containing a reagent and a reaction vessel for storing reaction liquid in which a sample and a reagent are mixed may be held. An external shape of these containers may be other than a cylindrical shape. In this case, a container holding member preferably has an appropriate shape along an external shape of a container to be held.

EXAMPLE 2

Figure 2A:
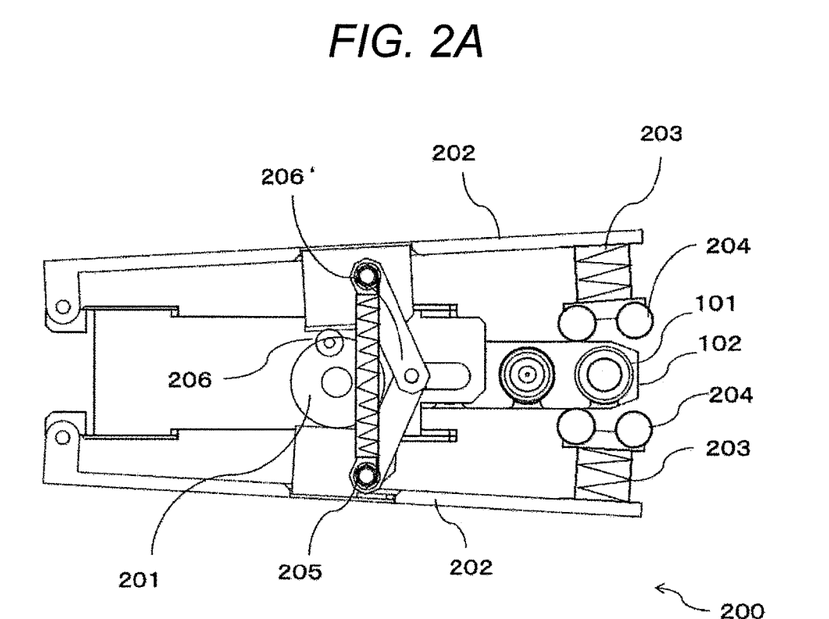
FIG. 2A is a view illustrating a state in which a holder using an arm opening/closing mechanism is opened by a rotational movement in an embodiment of the present invention.
Figure 2B:
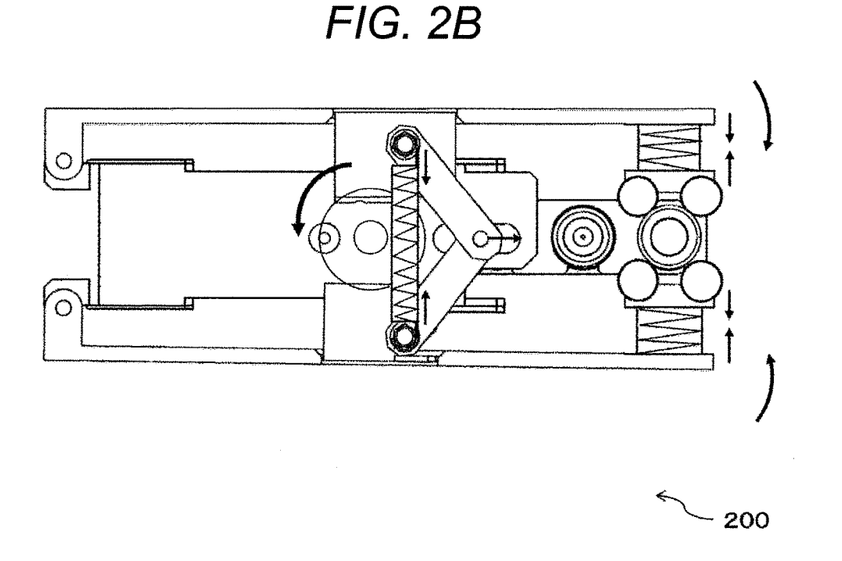
FIG. 2B is a view illustrating a state in which the holder using the arm opening/closing mechanism is closed by a rotational movement in the embodiment of the present invention.
Figure 2C:
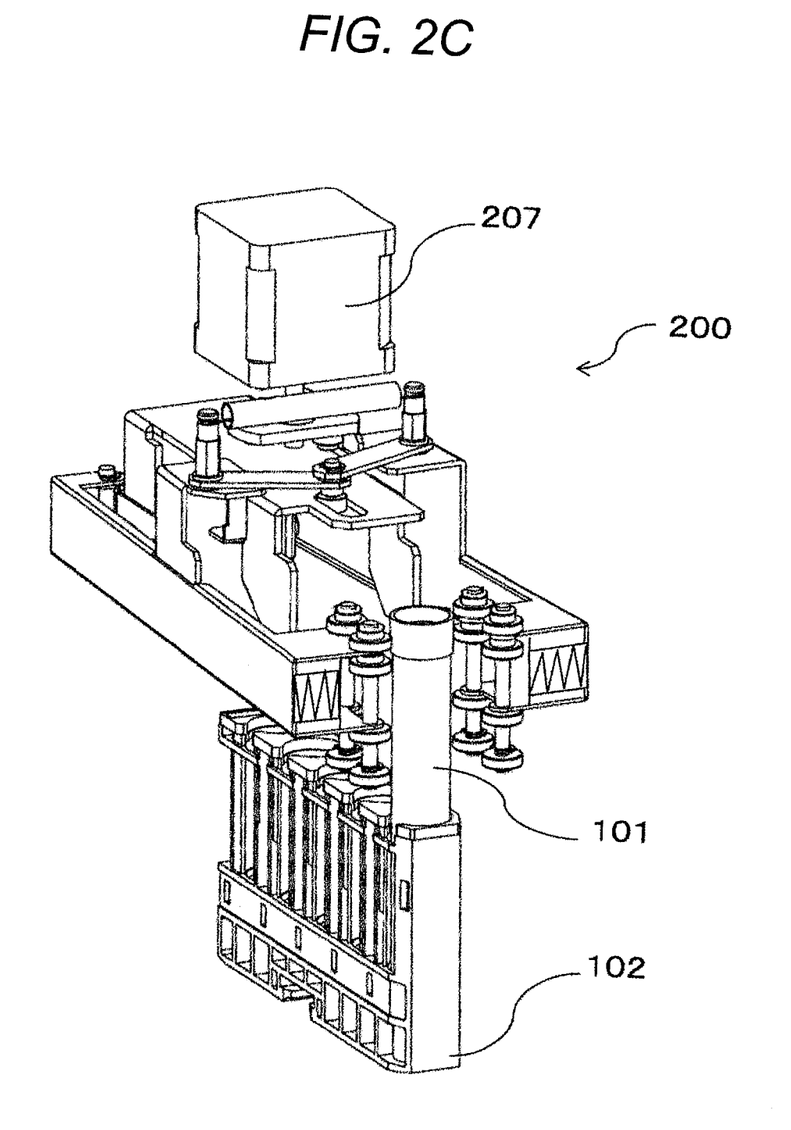
FIG. 2C is an overall view of the holder using the arm opening/closing mechanism by a rotational movement in the embodiment of the present invention.

As an embodiment of other examples according to the present invention, a container-clamping apparatus 200 using an arm opening/closing mechanism by a rotation movement will be described with reference to FIGS. 2A to 2C. A description overlapping with that in the Example 1 will be omitted. FIG. 2A illustrates a state in which the container-clamping apparatus 200 does not hold a container (an upper surface view). FIG. 2B illustrates a state in which the container-clamping apparatus 200 holds the container (an upper surface view). FIG. 2C illustrates a state in which the container-clamping apparatus 200 holds a container 101 (a perspective view).

The container holding device 200 includes an actuator 201, an opening/closing arm 202, an elastic body 203, a container holding member 204, a spring 205, and a motor 207. Power generated by rotation of the actuator 201 is transmitted to the opening/closing arm 202 through link mechanisms 206 and 206', and the opening/closing arm 202 is opened and closed on right and left sides. At this time, a container holding member is fixed at the rear of the mechanism in the opening/closing arm 202. Therefore, the container holding member rotationally drives so as to hold or release a container in association with driving of the actuator 201.

The container holding member 204 according to the example includes a roller mechanism. The roller mechanism includes a shaft extending in a length direction of a container and two rollers provided at both ends of the shaft, and two roller mechanisms are provided to each opening/closing arm.

When it is detected that a container 101 erected on a rack 102 to be held has arrived at a holding position of a container holder, a controller rotates the actuator 201 to shift the opening/closing arm 202 in an open state to a close state, and holds a container.

According to the example, effects similar to that in the example 1 can be realized by a different configuration, and even if a container position is deviated from a holding position, the center of the container can be held at all times and centered at the same position since the container is pushed by the same force from the both sides. Since a pressure is applied by an elastic body from both sides of the container, even if a diameter of the container is varied, the center of the container can be held at the same position.

Further, even if an external vibration such as device vibration is generated on a lateral direction, the vibration is absorbed by the elastic body 203, and the vibration is not transmitted to the held container.

EXAMPLE 3

In this example, a method for achieving an optimum centering function regardless of a container type will be described by using a container holding device 300.

Figure 3:
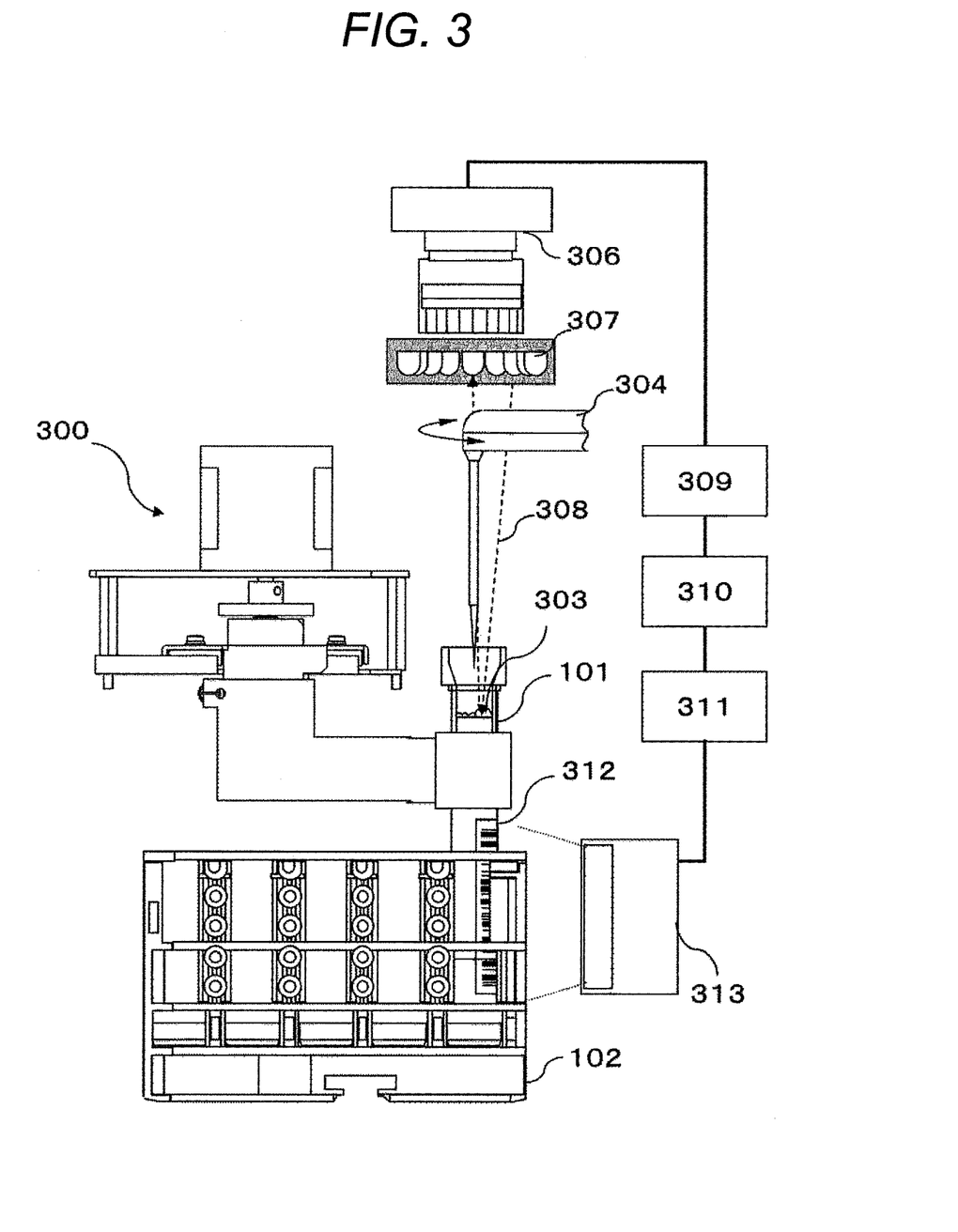
FIG. 3 is a configuration view of a sample checker including a container holding mechanism according to an embodiment of the present invention.

A bar code reader 313 illustrated in FIG. 3 reads a bar code 312 attached on a side surface of a container 101. Information for specifying a container type can be obtained from the bar code 112, and by inquiring the read information to a database stored in a device controller 311, information on the difference of the shape of the container 101 can be preliminary obtained from registered container information. Container shape information may be directly read from the bar code 312.

For example, by determining whether a diameter of the container 101 is φ16 mm or φ13 mm, a rotation frequency of an actuator provided to a container holder can be changed. For example, in the case where the container diameter is φ13 mm, the rotation frequency of the actuator is increased in comparison with a container having a diameter of φ16 mm. Consequently, an elastic body can be sufficiently compressed even while holding a small diameter container, and a holding force can be adjusted to the optimum force. Further, when a large diameter container is held, an excessive force is not applied, and the container is hardly damaged. Furthermore, a container can be held according to a shape such that effects by external vibration such as device vibration is suppressed. An arbitrary configuration written in other examples can be used in a specific configuration of the container holding device 300.

EXAMPLE 4

As an example of the present invention, a sample checker including a container holding device 300 according to the present invention will be described with reference to FIG. 3. The sample checker according to the example includes a function to detect foam on a liquid surface of a sample in a blood collection tube by an imaging means such as a camera before pipetting and analyzing the sample.

First, a configuration in the example will be described. A sample to be checked is erected on a rack 102 in a state in which the sample is put in a container 101 such as a blood collection tube and transported in an automatic analytical apparatus by using a transport means such as a belt conveyor. An apparatus which can transport, on a belt conveyor, a rack which can mount multiple containers will be exemplified in the example. However, the present invention is not limited to this embodiment. For example, in the apparatus, a sample disk which rotationally drives by arranging sample containers on the circumference and the sample checker may be combined. Further, the apparatus may separately carry a holder mounting one container on a belt conveyor.

A container type which can be used might be specified in some apparatus. However, according to user usage, multiple container types may be mixedly used. For example, a small container is used for a trace sample, and a container having a large internal volume such as a blood collection tube is used for a large volume sample. A small container may be erected at an opening of the blood collection tube.

A bar code 312 can be attached to a container 101 for identification, and such as a sample type can be recognized by reading the bar code 312 by a bar code reader 313. Other than the bar code, a two-dimensional code, an RFID tag, and an IC chip may be attached. In this case, a sample checker includes a reader corresponding to each storage medium.

Next, a sample check method using a container holding mechanism according to the example will be described.

A sample contained in the container 101 might have a foam 303 on a liquid surface. The foam 303 is generally visually confirmed before a user processes a sample, and the foam is appropriately removed by such as foam breaking. However, in the case where it is necessary to handle a large volume sample in a short time and in the case where preprocessing of a sample is automated by other system, it is difficult to totally remove the foam 303.

Generally, when an automatic analytical apparatus separates liquid of a sample and a reagent, an amount of a pipetting probe immersed in a target liquid is increased, an amount of remaining liquid on an outer wall of the pipetting probe is increased, and carrying to a target for a next separating operation (cross-communication) is increased. To avoid such issue, a pipetting probe is used which has a probe mounting a function to detect a position of a liquid surface by measuring, in real time, a change in a physical quantity of such as a resistance, a capacitance, an inner pressure in a probe, and a probe vibration frequency, which are a physical quantity changed when coming into contact with a liquid surface to reduce an immersed amount of the pipetting probe. A liquid surface detection is used to minimize an immersed contamination amount of a pipetting probe 304 and is an essential function in an automatic analytical apparatus since there are various types of sample containers 101, and an amount of filled sample is not fixed. However, a conventional liquid surface detection function cannot distinct the foam 303 as a liquid surface. In this case, a film and a foam are incorrectly determined as a liquid surface, and suction is performed without coming into contact with an analysis target. Therefore, an originally needed amount is not separated, and an accurate analysis result may not be output.

Therefore, in the example, foam is detected by an imaging unit 306 at a sample separating position (a position for temporary stop) for separating a sample. Specifically, a lighting 307 is irradiated from upward at a position for temporary stop for separating a sample. The imaging unit 306 is provided on an upper side of a blood collection tube as well as the lighting 307 and images a reflected light which is a light returned when a lighting light 308 from the lighting 307 reflects on a target sample liquid surface. Regarding the lighting 307 and the imaging unit 306, for example, the lighting 307 may be a white light source, and the imaging unit may be a camera which images an image of a liquid surface. Further, the lighting may be a laser light, and the imaging unit may be a light receiving element obtaining a reflected light from a liquid surface. An image analysis unit 310 detects foam on a sample liquid surface in a container by image-processing an obtained image. A position where the imaging unit is provided is not limited to an upper side of a blood collection tube, and the imaging unit may be provided on a side, a lower side, or an oblique upper side of the blood collection tube.

In the case where foam is detected, it is notified to the device controller 311, and the device controller 311 determines that sample separating by the pipetting probe 304 is "negative". Consequently, the device controller 311 carries the container on an abnormal sample tray. In the case where foam is not detected and in the case where foam is detected at a position where does not affect the separating operation, sample separating by the pipetting probe 304 is determined as "possible", and the device controller 311 carries the container on a normal sample tray or carries the container to a separation device through a transport line. The imaging unit 306 is generally image-photographing by a camera. However, the unit can be replaced to a variation measurement of a target by a laser.

Generally, as the container 101 to be used, various containers are used depending on a purpose as described above. In the case where a centroid position of the container 101 mounted on the rack 102 is low, the container is stable in a state mounted on the rack and hardly affected by external vibration such as device vibration. However, in the case where a centroid position of the container 101 is high with respect to the rack 102, such as in the case where a large volume of specimens are contained in a container and in the case where a small container containing liquid is erected at an opening of an empty blood collection tube, the container is easily affected by external vibration such as device vibration. If a container is vibrated by external vibration during imaging, an image obtained for sample check is likely to be blurred, and foam might be erroneously detected.

Therefore, in the case where it is realized that a centroid position of the container 101 is high with respect to the rack 102 by reading information stored in the bar code 312 by the bar code reader 313, the container 101 is held by the container-clamping apparatus 300 when the container 101 is imaged to suppress blurring by external vibration such as device vibration on the image obtained for sample check. The container may be controlled so as to be held at all times without having a process to detect a container type.

By including the container-clamping apparatus 300 according to the present invention in a sample checker, the center of a container is positioned at the same position regardless of a container type. Therefore, existence and a position of a foam can be accurately detected when foam is detected. Further, in a state in which device vibration may occur during sample check, the sample checker can suppress a deviation of a liquid surface position by the vibration and accurately detect a state of foam on a liquid surface.

EXAMPLE 5

Figure 4:
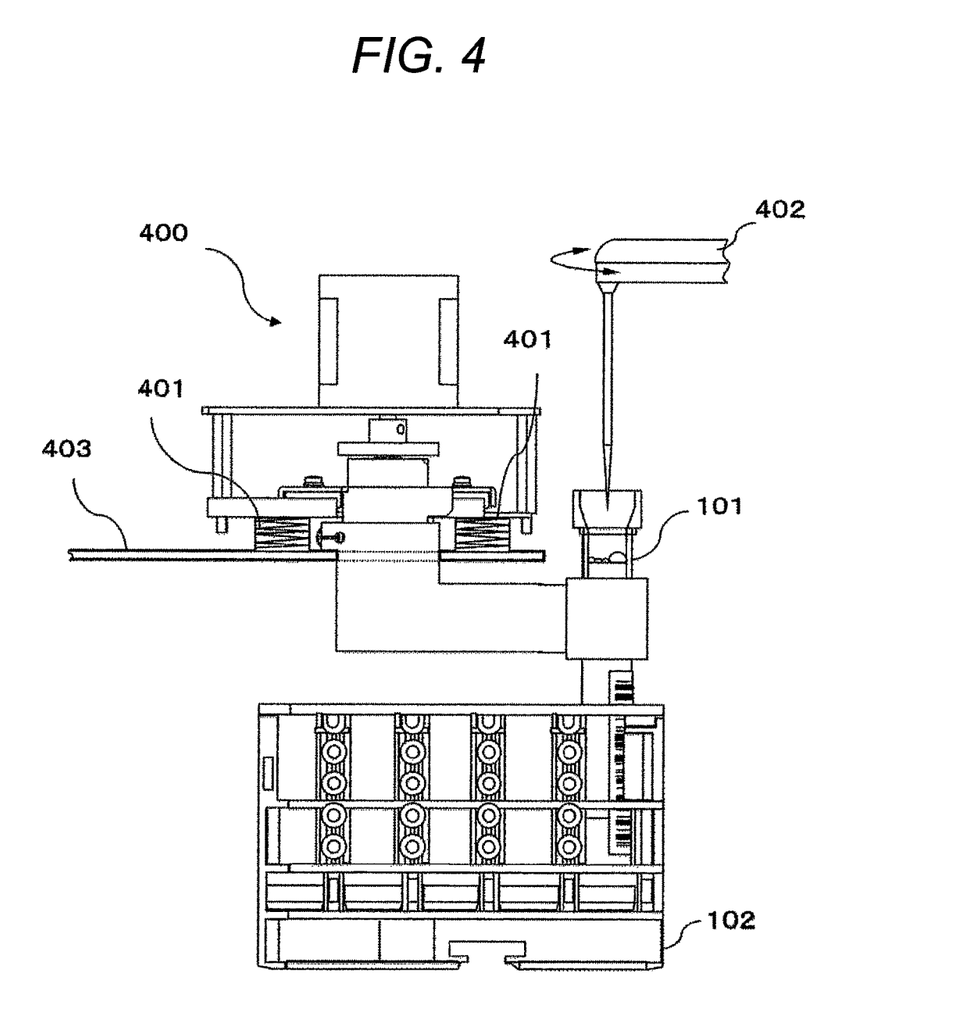
FIG. 4 is a configuration view of an automatic analytical apparatus using a vibration suppression mechanism between a holder and a holder attachment unit in another embodiment of the present invention.

As another example of the present invention, a pipetting device including a container holding device 400 will be described with reference to FIG. 4. A description will be omitted regarding a content which is not changed from other examples.

The pipetting device in the example moves a probe 402 downward in a container and suctions a predetermined amount of samples from the vicinity of a sample liquid surface when a sample container mounted on a carried rack is carried at a pipetting position. The probe 402 which has been suctioned the sample moves upward and comes out of the container. Then, the probe 402 discharges the suctioned sample by a rotation movement or a horizontal movement in a reaction vessel (not illustrated) disposed at other position. Consequently, the predetermined amount of samples can be separated in another container.

In the case where the pipetting probe 402 having a liquid surface detection function separates liquid, to minimize an immersed contamination amount of the pipetting probe, a sample is generally separated at a position where the pipetting probe moves downward by a predetermined amount after detecting a liquid surface position. However, in the case where external vibration occurs when the pipetting probe is moving downward, a liquid surface moves by vibration, and detecting an accurate liquid surface position may be difficult. Further, even if the pipetting probe accurately detects a liquid surface position, a side area of a probe coming into contact with a sample is increased when the liquid surface moves by vibration after detection, and contamination by suctioning a next sample liquid in a state in which a sample is attached on a side surface of the probe may increasingly occur.

The container holding device 400 according to the example includes an elastic body 401 between with a container-clamping apparatus attachment unit 403 for attaching the container holding device to a case of a pipetting device. Therefore, even if an elastic body is not provided between an opening/closing arm of the container holder 400 and a container holding mechanism, effects by external vibration is absorbed by the elastic body 401, and therefore a configuration of the container holding device 400 can be simplified.

According to the example, an elastic body 201 is provided between the container holding device 400 and the container holder attachment unit 403, and therefore, in comparison with the case where the elastic body is provided at a tip of the container-clamping apparatus 400, the elastic body can be disposed on a wide area, and vibration can be effectively suppressed.

Further, since the container-clamping apparatus 400 stably clamps a container at a pipetting position, even in the case where external vibration occurs when a sample is separated, it can be prevented that the vibration is transmitted to liquid in a container. Consequently, a liquid surface does not vibrate when a pipetting probe moves downward, and pipetting accuracy is stabilized. The container holding device according to the example may be replaced to a configuration described in other examples according to the present invention.

EXAMPLE 6

As another example of the present invention, an automatic analytical apparatus including a container-clamping apparatus 105 will be described. Examples of the automatic analytical apparatus include, but not limited to, various type apparatuses, such as a biochemical analytical apparatus, an immune analytical apparatus, a coagulation analytical apparatus. In the example, the case of applying the immune analytical apparatus will be described.

Figure 5:
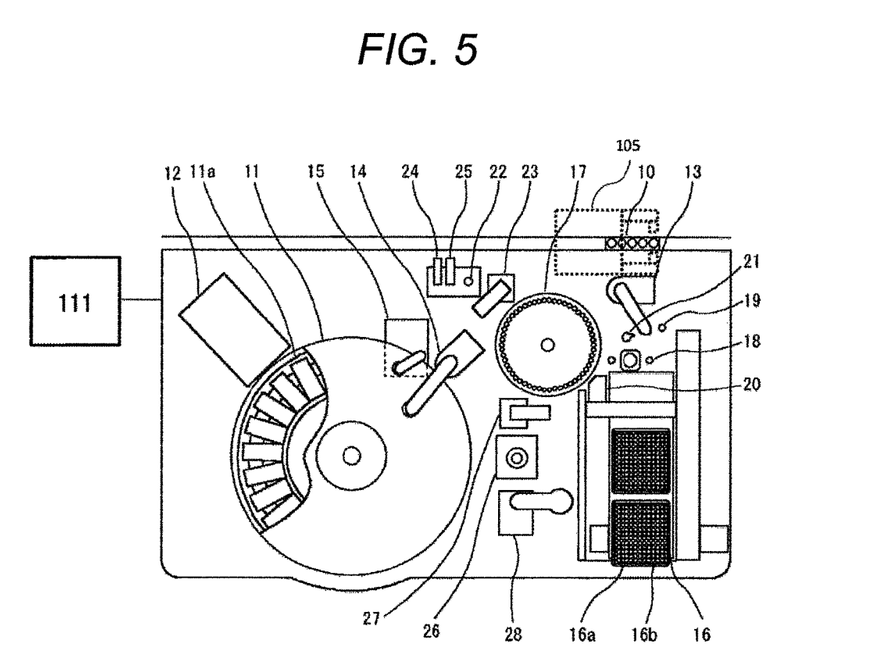
FIG. 5 is an overall view of the automatic analytical apparatus including the container holding mechanism according to the present invention.

First, the basic configuration and operation of the automatic immune analytical apparatus will be described with reference to FIG. 5. The automatic immune analytical apparatus includes such as a sample rack 10, a reagent disk 11, a container lid opening/closing mechanism 12, a sample pipetting mechanism 13, a reagent pipetting mechanism 14, a magnetic particle agitation mechanism 15, a magazine 16, a reaction tank 17, a transport mechanism 20, a chip discarding unit 21, a transport mechanism 23, an impurity suction mechanism 24, a washing liquid discharging mechanism 25, a transport mechanism 27, and a reagent discharging mechanism 28. A sample is placed on the sample rack 10. The reagent disk 11 stores a reagent container 11a having a lid, which contains a reagent and magnetic particles needed in an immune reaction. The container lid opening/closing mechanism 12 opens and closes a lid of the reagent container 11a having the lid. The sample pipetting mechanism 13 pipets and separates a sample. The reagent pipetting mechanism 14 pipets and separates a reagent and magnetic particles from the reagent container 11a having a lid. The magnetic particle agitation mechanism 15 agitates magnetic particles in the reagent container 11a having a lid. The magazine 16 stores a reaction vessel 16a (hereinafter called a vessel) to be used in reaction and a chip 16b to be used for pipetting and separating a sample. The reaction tank 17 can control a temperature to react a sample and a reagent in the vessel 16a. The transport mechanism 20 transports the vessel 16a to the reaction tank 17 and a vessel discarding unit 18 and transports the chip 16b to a buffer 19 which temporarily stores a sample for pipetting. The chip discarding unit 21 discards the chip 16b used for pipetting of the sample. The transport mechanism 23 transports the vessel 16a from the reaction tank 17 to a magnetic separator 22 or from the magnetic separator 22 to the reaction tank 17. The impurity suction mechanism 24 suctions liquid including impurities in the vessel 16a transported by the magnetic separator 22. The washing liquid discharging mechanism 25 discharges washing liquid in the vessel 16a transported to the magnetic separator 22. The transport mechanism 27 transports the vessel 16a from the reaction tank 17 to a detection unit 26 or from the detection unit 26 to the reaction tank 17. The reagent discharging mechanism 28 discharges a reagent for detection to the vessel 16a transported to the detection unit 26.

Next, a standard operation will be described. First, by the transport mechanism 20, the vessel 16a is transported on the reaction tank 17 from the magazine 16, and also the chip 16b is transported to the buffer 19. The reaction tank 17 rotates, and the transported vessel 16a moves to a reagent pipetting position. By the reagent pipetting mechanism 14, a reagent is pipetted from the reagent disk 11 to the vessel 16a on the reaction tank 17.

The reaction tank 17 rotates again, and the vessel 16a moves to the sample pipetting position. The chip 16b transported to the buffer 19 is mounted to a chip holder by an upward and downward operation of the sample pipetting mechanism 13, and a sample is separated from the sample rack 10 and pipetted to the vessel 16a moved to the sample pipetting position. The used chip 16b is discharged to the chip discarding unit 21 by an upward and downward operation of the sample pipetting mechanism 13.

The vessel 16a in which a sample and a reagent have been pipetted moves to a reagent pipetting position by reaction of the reaction tank 17 after waiting for a reaction for a certain period of time in the reaction tank 17, and magnetic particles are pipetted and separated from the reagent disk 11 by the reagent pipetting mechanism 14. Further, after waiting for a reaction for a certain period of time in the reaction tank 17, the reaction tank 17 rotates, and the vessel 16a on the reaction tank 17 is transported to the magnetic separator 22 by the transport mechanism 23.

To separate magnetic components including reaction products and non magnetic components including impurities in the vessel 16a, the magnetic separator 22 repeats suctioning by the impurity suction mechanism 24 and discharging washing liquid by the washing liquid discharging mechanism 25 several times. Consequently, magnetic components including reaction products are remained in the vessel 16a, and the vessel 16a is returned to the reaction tank 17 by the transport mechanism 23

After the reaction tank 17 rotates, and the vessel 16a is transported to the detection unit 26 by the transport mechanism 27, a reagent for detection is discharged by the reagent discharging mechanism 28 to the vessel 16a, and detection is performed. The vessel 16a which has been detected is returned to the reaction tank 17 by the transport mechanism 27, the reaction tank 17 rotates, and the vessel 16a is discarded to the vessel discarding unit 18 by the transport mechanism 20. After that, the above-described operation is repeated to a sample to be used.

The container-clamping apparatus 105 according to the example is provided on an upper side of a position where the sample pipetting mechanism 13 separates a sample from the sample rack 10. By providing the container-clamping apparatus at this position, while separating a liquid surface of the transported sample, vibration caused by operations by other mechanisms in an automatic immune analytical apparatus is not transmitted to a sample, and the sample can be accurately separated.

Further, the immune analytical apparatus may include a sample check mechanism. Existence of foam on a liquid surface can be checked by irradiating a lighting light and a laser light to a sample liquid surface for sample check and by checking a reflected light from a liquid surface by an imaging unit such as a camera and a light detector. By holding a container by the container-clamping apparatus according to the example for sample check, vibration caused by operations by other mechanisms is not transmitted to a sample during the sample check, a state of a liquid surface can be accurately checked. In this case, the sample check mechanism is preferably provided at a position which is same as a pipetting position by the sample pipetting mechanism or an upper stream side than the position. In the case where a pipetting position and a sample check position are the same, a container holder according to the present invention can be commonly used, and a number of mechanisms can be decreased.

Further, the container-clamping apparatus 105 according to the example may hold a reagent container at a position where the reagent pipetting mechanism 14 pipets a reagent contained in a reagent container and a position where the magnetic particle agitation mechanism 15 agitates a reagent. In this case, effects on a reagent by vibration caused by operations of peripheral mechanisms can be suppressed, and the reagent can be separated and agitated always in the same state.

Further, the container holder according to the example may hold the vessel 16a at a suction position by the impurity suction mechanism 24 which separates impurities other than magnetic particles in the vessel 16a containing reaction liquid. In this case, impurities can be removed in the vessel always in the same state.

EXAMPLE 7

In the example, other embodiment of a container-clamping apparatus using an arm opening/closing mechanism by a liner movement which can position the center of a container will be described with reference to FIGS. 6A to 6C. A description overlapping with that in the Example 1 will be omitted.

Figure 6A:
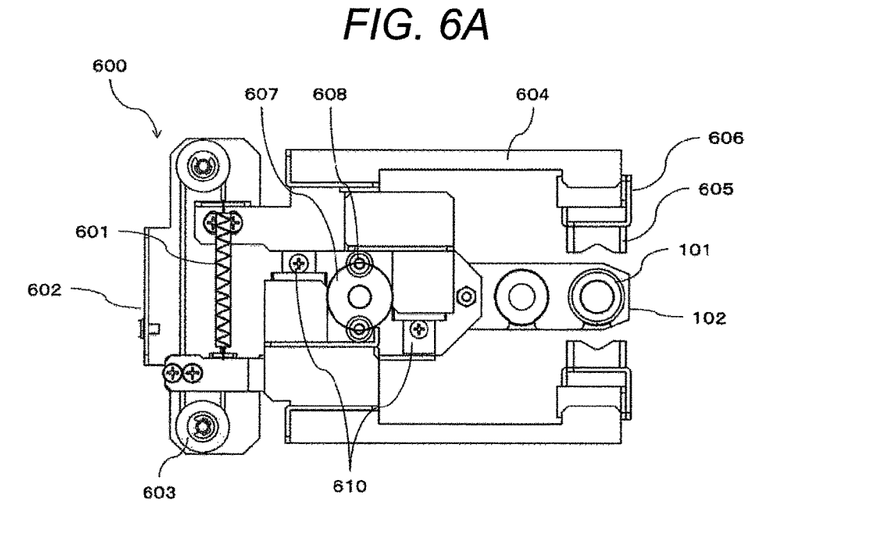
FIG. 6A is a view illustrating a state in which a holder using an arm opening/closing mechanism is opened by a linear movement in which the center of a container can be predominantly positioned in an embodiment of the present invention.
Figure 6B:
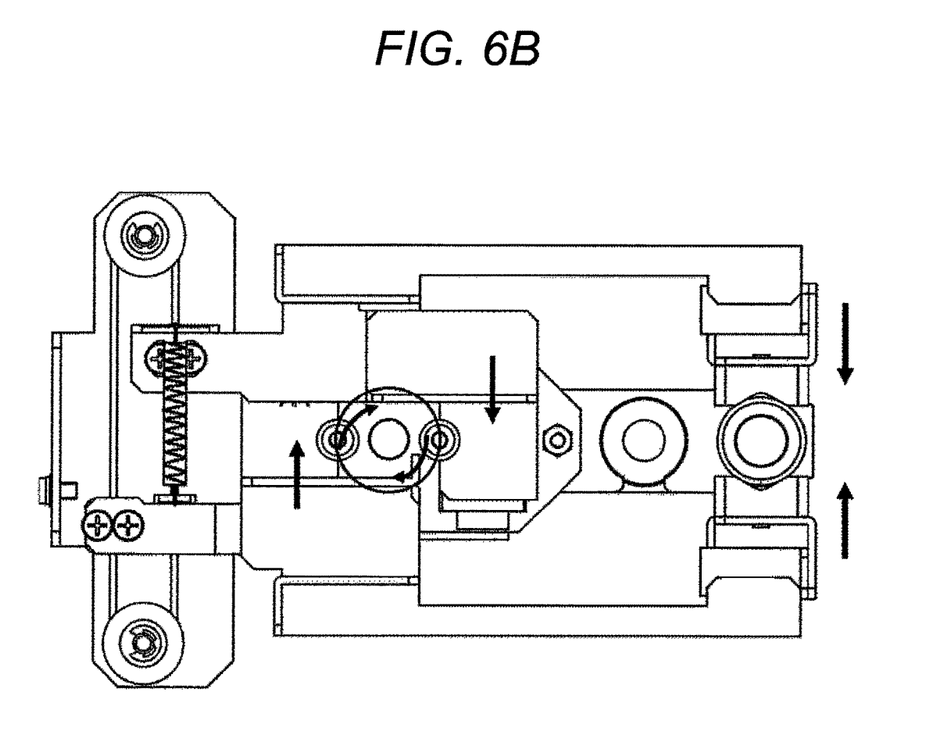
FIG. 6B is a view illustrating a state in which the holder using the arm opening/closing mechanism is closed by a linear movement in which the center of a container can be predominantly positioned in the embodiment of the present invention.
Figure 6C:
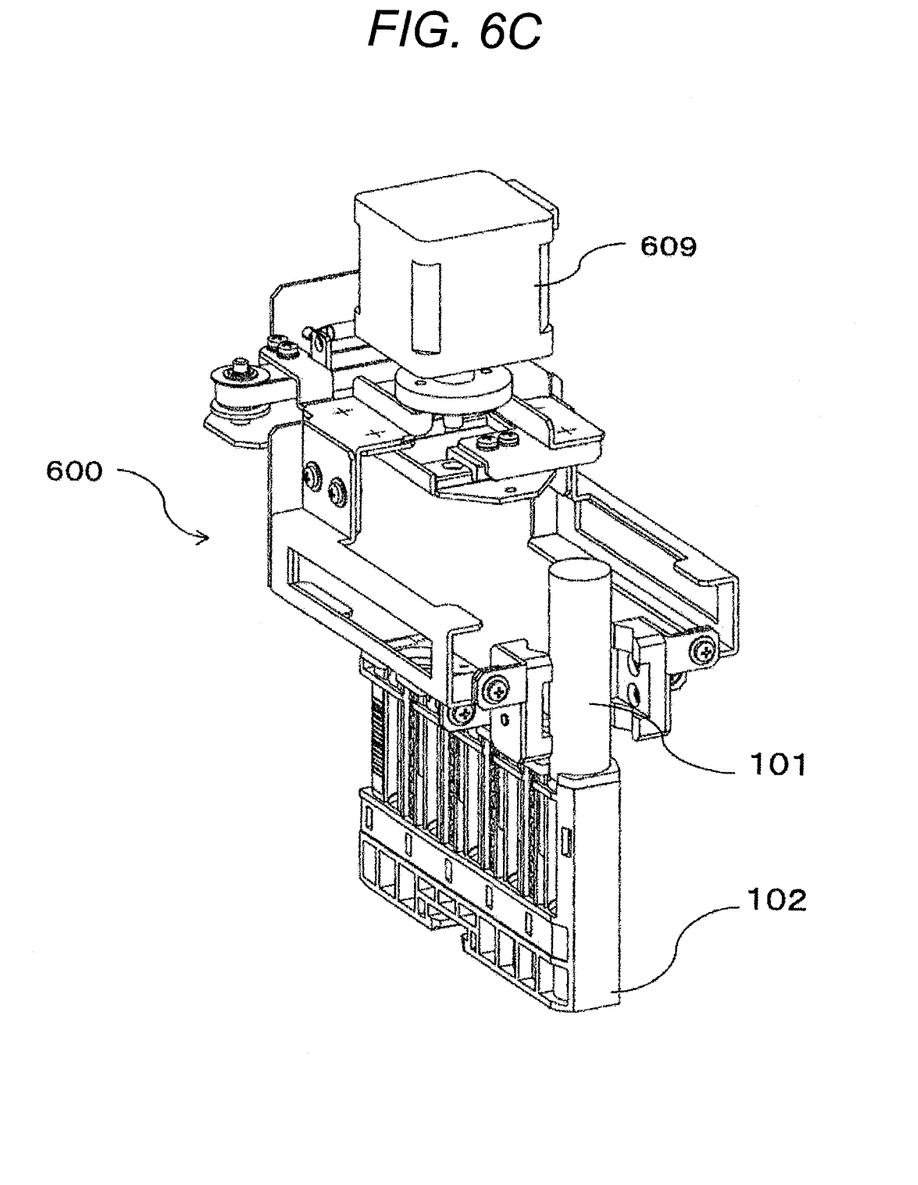
FIG. 6C is an overall view of the holder using the arm opening/closing mechanism by a linear movement in which the center of a container can be predominantly positioned in the embodiment of the present invention.

FIGS. 6A and 6B are views illustrating a container holder from an upper surface side. FIG. 6A illustrates a state in which the container holder is not holding a container. FIG. 6B illustrates a state in which the container holder is holding the container. FIG. 6C illustrates an overall view of the container holder and a container 101 erected on a rack 102 as an example of a holding target.

A basic configuration and an operation outline of the container-clamping apparatus 600 are similar to those in the Example 1. However, a spring 601, a belt 602, and a pulley 603 which support a liner movement are added in comparison with the Example 1. Further, a container holding member 605 and a connection member 606 for connecting the container holding member 605 to an opening/closing arm 604 are provided to a tip of the opening/closing arm 604. In the example, the connection member 606 is formed of a rigid material.

In the example, at least a part of the container holding member 605 is formed of an elastic body such as rubber, and therefore, a centering function of a container described in the Examples 1 and 2 can be achieved by which the elastic body portion is compressed when the container is held. A whole of the container holding member 605 may be formed of an elastic body, or a part of the member may be formed of an elastic body, and other parts may be formed of a rigid member. When power from the opening/closing arm 604 is transmitted to a container, the container is compressed. Therefore, at least a region between the rigid member 606 and the container holding member 605 includes a region formed of an elastic body.

Power generated by rotation of an actuator 607 by a motor 609 is transmitted to the opening/closing arm 604 via a link mechanism 608, and the opening/closing arm 604 is opened and closed on right and left sides by a linear movement mechanism 610. At this time, the belt 602 attached via the pulley 603 and the right and left opening/closing arms 604 are connected, and power for opening and closing is transmitted each other via the belt by opening and closing the opening/closing arm 604. Therefore, an operation amount of both opening/closing strokes in an arm opening/closing operation by a liner movement becomes uniform, and the center position can be stably and easily positioned by a uniform force when the container 101 is held via the container holding member 605.

REFERENCE SIGNS LIST

100, 200, 300, 400, 600 container-clamping apparatus
101 container
102 rack
103, 201 actuator
104, 202 opening/closing arm
105, 203 elastic body
106, 204 container holding member
107 linear movement mechanism
108, 206 link mechanism
109, 207 motor
303 foam
304, 402 probe
306 imaging unit
307 lighting
308 lighting light
309 imaging controller
310 image analysis unit
311 device controller
312 bar code
313 bar code reader
401 elastic body
403 container holder attachment unit
601 spring
602 belt
603 pulley
604 opening/closing arm
605 container holding member
606 connection member
607 actuator
608 link mechanism
609 motor

The invention claimed is:

1. An automatic analytical apparatus, comprising:
a detection unit;
a bar code reader;
a controller connected to the bar code reader;
a probe configured to suction liquid to be used in an analysis;
a transport apparatus configured to transport a container having a cylindrical shape and containing the liquid;
a container-clamping apparatus configured to clamp the container carried by the transport apparatus; and
an imaging device configured to image a liquid surface of the liquid which is any of a biological sample, a reagent, or a mixture of the biological sample and the reagent;

wherein the container-clamping apparatus clamps the container at a position where the imaging device obtains an image,
wherein the container-clamping apparatus comprises:
  at least two container holding members configured to hold a side wall of the container;
  at least two arms respectively configured to move the at least two container holding members toward the container; and
  at least two connection members respectively positioned between the at least two arms and the at least two container holding members; and
  an actuator that drives, by rotation of the actuator, the at least two arms in at least a horizontal direction,
wherein at least a part of the at least two connection members includes an elastic body for suppressing vibration of the container and centering the container upon clamping of the container,
wherein each of the at least two container holding members includes a recess to hold the container having the cylindrical shape, and
wherein the controller is connected to the actuator and is programmed to:
  read information, by the bar code reader, from a label on the container,
  obtain information of a diameter of the container based on the information read by the bar code reader,
  drive the actuator based on the obtained information of the diameter of the container, and
  control a rotation frequency of the actuator based on the obtained information of the diameter of the container to provide sufficient compression of the elastic body when holding the container.

2. The automatic analytical apparatus according to claim 1, wherein the controller is programmed to determine whether foam is present on the liquid surface based on the image imaged by the imaging device.

3. The automatic analytical apparatus according to claim 1, wherein the controller is further programmed to:
  control the rotation frequency of the actuator to be greater for the container relative to another rotation frequency applied for another container having a larger diameter.

* * * * *